United States Patent [19]

Schübel

[11] 4,445,088
[45] Apr. 24, 1984

[54] METHOD AND ARRANGEMENT FOR EVALUATING A DEFECT SIGNAL BY COMPARING THE RATIO OF MAXIMUM SIGNAL RISE AND MAXIMUM SIGNAL MAGNITUDE TO A PREDETERMINED VALUE

[75] Inventor: Winfried Schübel, Pliezhausen, Fed. Rep. of Germany

[73] Assignee: Institut Dr. Friedrich Förster Prüfgerätebau, In Laisen, Fed. Rep. of Germany

[21] Appl. No.: 257,763

[22] Filed: Apr. 27, 1981

[30] Foreign Application Priority Data

May 10, 1980 [DE] Fed. Rep. of Germany ....... 3017979

[51] Int. Cl.³ ............................................. G01N 27/82
[52] U.S. Cl. ..................................... 324/238; 324/240
[58] Field of Search ................................. 324/236–243, 324/225; 364/485, 487, 571; 307/231

[56] References Cited

U.S. PATENT DOCUMENTS

| | | | |
|---|---|---|---|
| 2,925,552 | 2/1960 | Cowan et al. | 324/217 |
| 4,117,403 | 9/1978 | Forster et al. | 324/240 |
| 4,330,748 | 5/1982 | Holden | 324/225 |

*Primary Examiner*—Gerard R. Strecker
*Assistant Examiner*—Walter E. Snow
*Attorney, Agent, or Firm*—George J. Netter

[57] ABSTRACT

Voltage signals induced in a magnetic probe by stray flux at the location of a defect in a test piece are monitored determining the maximum signal magnitude and maximum signal rise. A quotient of the maximum rise and magnitude is formed and compared with a predetermined threshold value. The sample rate of rise and magnitude is functionally related to the scanning speed thereby providing accuracy independent of the scanning speed.

4 Claims, 3 Drawing Figures

METHOD AND ARRANGEMENT FOR EVALUATING A DEFECT SIGNAL BY COMPARING THE RATIO OF MAXIMUM SIGNAL RISE AND MAXIMUM SIGNAL MAGNITUDE TO A PREDETERMINED VALUE

The present invention relates generally to magnetic stray field testing for defects, and, more particularly, to a method and arrangement for evaluating an electric signal generated at the location of a defect by a magnetic stray flux probe uniformly scanning a magnetized test piece to determine the location of the defect relative to the surface of the test piece.

BACKGROUND OF THE INVENTION

Apart from the location of defects and the determination of their size, it is often important in stray-flux testing to determine the position of the defects relative to the test piece surface. Generally, past known methods made use of the fact that signals derived from defects located at different positions relative to the test piece surface, i.e., the signals derived from exterior and interior defects of pipes, exhibit different frequency spectrums. So the frequency characteristics of the signal of an exterior defect are for instance considerably higher than those of an interior defect. According to a known method described in U.S. Pat. No. 4,117,403, the stray-flux signals obtained when scanning a pipe with a stray flux probe are split up into two channels, one including all signals, whether derived from exterior or from interior defects, while the other channel discriminates between signals according to their different frequency ranges, using for instance, a high-pass. The signals of the two channels are stored temporarily, and the amplitudes of the stored signals are used to discern between interior or exterior defects. This may be accomplished, for example, by forming the quotients of the signals of the two channels after having adjusted the amplification of the two channels in a manner such that an exterior defect will cause the two channels to supply signals of the same amplitude, i.e., give a quotient "1" while an interior defect which as a result of its lower frequency range is attenuated in the high-pass giving a smaller quotient clearly discernible from "1". Although in practice this procedure has proven satisfactory in many cases, it has been found disadvantageous that apart from the necessary mutual adaptation of the two channels, every new test requires a readjustment of the frequency-dependent element in the second channel which as a rule consists of a high-pass. This adjustment is difficult and requires an excessive amount of time for accomplishment, even though the operator may be experienced.

OBJECT AND SUMMARY OF THE INVENTION

It is, therefore, a primary object of the present invention to provide a method and an arragement for implementing the method, in which only a single signal channel is required and thereby eliminates the necessity to adjust a frequency-dependent element.

In accordance with the practice of the present invention evaluation of the frequency information of a defect signal is achieved in a simple manner and independently of the amplitude of the defect signal. The frequency-dependent element required heretofore, which in most cases consisted in a high-pass, is not used, a fact which considerably simplifies adjustment. By determining, in accordance with a further improvement of the invention, momentary values of the signal voltage at n uniformly spaced points of the defect signal, one gains in a simple manner the means to form with sufficient accuracy the values for the maximum rise of the defect signal voltage and for the maximum defect signal voltage. According to another aspect of the invention, the evaluation process is started at the moment when the defect signal voltage exceeds a given threshold value which may also be identical with the threshold value defining the smallest defect to be measured. To obtain full use of the leading edge of the defect signal, in a still further aspect of the invention, momentary values of the defect signal are continuously buffered and such buffered momentary values are used to form the quotient. In addition, the intervals $\Delta t$ between the determinations of the momentary values are derived from a pulse frequency functionally related to the scanning speed of the test unit, and this provides for the first time complete independence from the scanning speed which may differ from case to case and may be subject also to operational variations.

DESCRIPTION OF PREFERRED EMBODIMENTS

Figure 1:
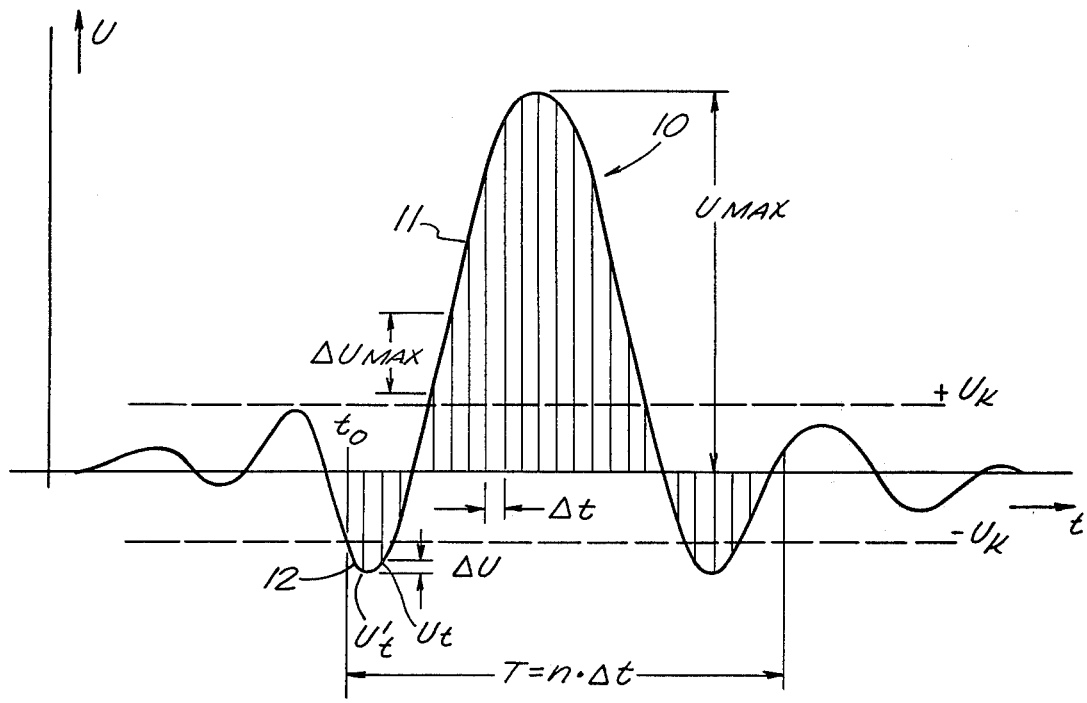
FIGS. 1 and 2 show diagrammatic representations of a defect signal.

FIG. 1 shows the development of a signal voltage U(10) of a defect in a magnetized test piece which is induced by the stray flux of the defect and sensed by a stray flux probe when the latter passes the defect. The maximum signal voltage $U_{max}$ is clearly related to the size of the defect from which it originates. To determine whether or not a defect is to be regarded as acceptable, the maximum signal voltage is compared with a given threshold voltage. In the present case, the threshold voltage $U_K$ which applies to both positive and negative voltages, serves at the same time to define the beginning of the evaluation process which commences when this threshold value is exceeded. Given the fact that digital values lend themselves particularly well to the evaluation process, it will be assumed for the purposes of the following description that the defect signal 10 is converted into digital values by means of an analog-to-digital converter. As will be shown, when the threshold value $U_K$ is exceeded at the moment $t_o$, the system starts to subdivide an evaluation period T which extends over and beyond the defect signal 10, into n equal sections $\Delta t$. To this end, the analog-to-digital converter is controlled by a fixed pulse frequency $f_T$ with a cycle $\Delta t$. At the end of every cycle $\Delta t$, a momentary value $U_t$ is determined, and at the same time the difference $\Delta U = U_t - U'_t$ is formed between $U_t$ and $U'_t$. The method of determining the maximum value of the n values $U_t$ is as follows: The value of every $U_t$ is compared to that of a preceding $U'_t$. In doing so, negative values of $U_t$ are multiplied by $(-1)$, which operation corresponds to rectification. If the value of the preceding $U'_t$ is greater than that of $U_t$, $U'_t$ is retained as peak value, and the next $U_t$ value is compared with this latter peak value $U_t$. The peak value retained at the end of the n sections $\Delta t$ is retained as $U_{max}$. The same method is used to determine from among the n differences, $\Delta U$ the maximum value $\Delta U_{max}$ which, considering the given equality of each Δt, represents the approximate value of the maximum rise of the defect signal voltage $(\Delta U/\Delta t)_{max}$. The quality of the approximation of $(\Delta U/\Delta t)_{max}$ and $\Delta U_{max}$ to the real maximum value of the defect signal voltage rise and/or the real maximum value of the defect signal voltage itself depends on the selected number n. In many cases, for example, the number n=25 used in the present example, should be sufficient. The two maximum values $\Delta U_{max}$ and $U_{max}$ retained at the end of the evaluation period T are used to form the quotient Q=ΔU max/U max.

This quotient represents a defect parameter which is independent of the value of the defect signal 10, i.e., of the size of the defect and the amplification value of the test channel connected to the outlet end of the test probe. In contrast, the parameter Q is clearly indicative of the form of the defect signal, i.e., its frequency spectrum. It is this quotient that enables the described arrangement to determine the position of a defect relative to the surface and, in particular, to resolve the question "interior or exterior defect". In order to decide this latter question, the quotient Q is compared with a threshold value situated between the Q values obtained for interior defects and those obtained for exterior defects. The decision interior defect or interior defect now depends on whether or not this threshold has been exceeded. For instance, the ratio of 1:4 may be regarded as a typical ratio between the quotients of an interior defect and those of an exterior defect, for a wall thickness of approximately 10 mm. If one assumes that the path S of induction of the defect signal into an induction probe having a base width of 5 mm is equal to 10 mm, and if one further assumes a scanning speed of $V_a=2$ m/sec., the following useful calculated values are obtained:

$$\text{evaluation period } T = \frac{s}{V_a} = 5 \text{ m sec.}$$

$$\text{evaluation sections } \Delta t = \frac{T}{n} = 200 \text{ μsec.}$$

$$\text{pulse frequency } f_T = \frac{1}{\Delta t} = 5 \text{ Khz}$$

Figure 2:
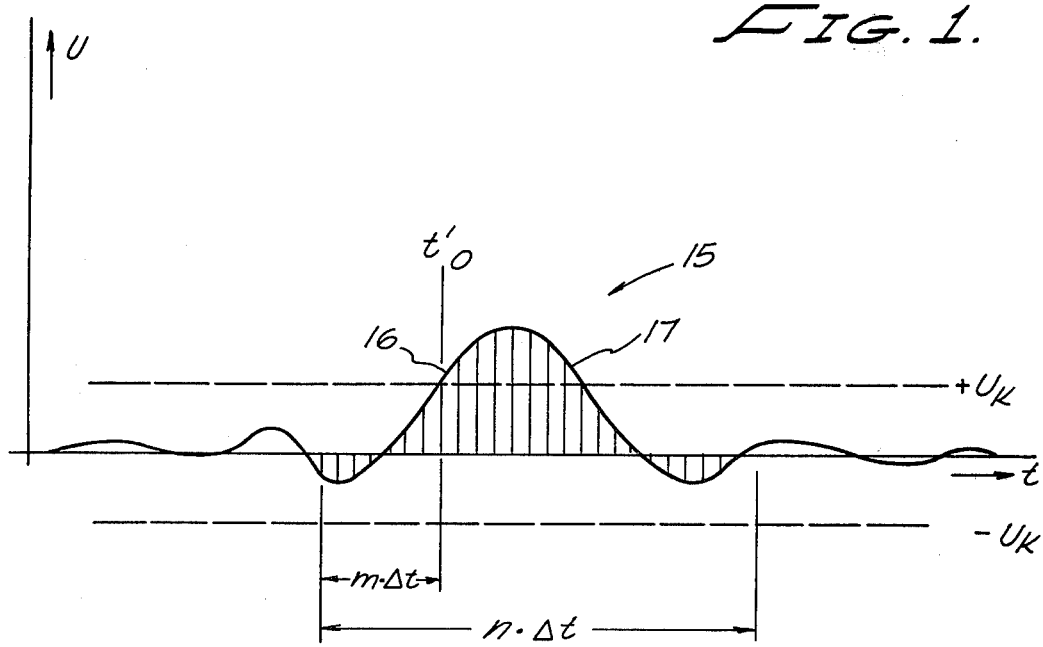

In the case of the defect signal 10 represented in FIG. 1, the threshold value $U_K$ has been exceeded by a negative signal portion 12 preceding the leading positive edge 11. Thus, the whole leading edge 11 is covered by the evaluation period T. In the event of the same threshold value $U_K$ and a defect signal of lower value, as for instance the defect signal 15 represented in FIG. 2, the threshold voltage is exceeded at a later moment $t'_o$ coinciding with the middle of the leading edge 16 of the defect signal 15. This means, however, that only the trailing edge 17 of the defect signal 15 is available for evaluation as the value of the maximum rise of the forward edge 16 may have been obtained before the moment $t'_o$. This condition is very undesirable, especially in cases of dissymmetrical defect signals. In order to permit any momentary values obtained before the moment $t'_o$ to be included into the evaluation so that both edges of the defect signal 15 can be evaluated, a certain number of momentary values are buffered continuously and at equal intervals Δt. These buffered momentary values are available at the moment $t'_o$ when the evaluation commences to start the evaluation with a momentary value that had been obtained a period of time m·Δt before the moment $t'_o$.

Figure 3:
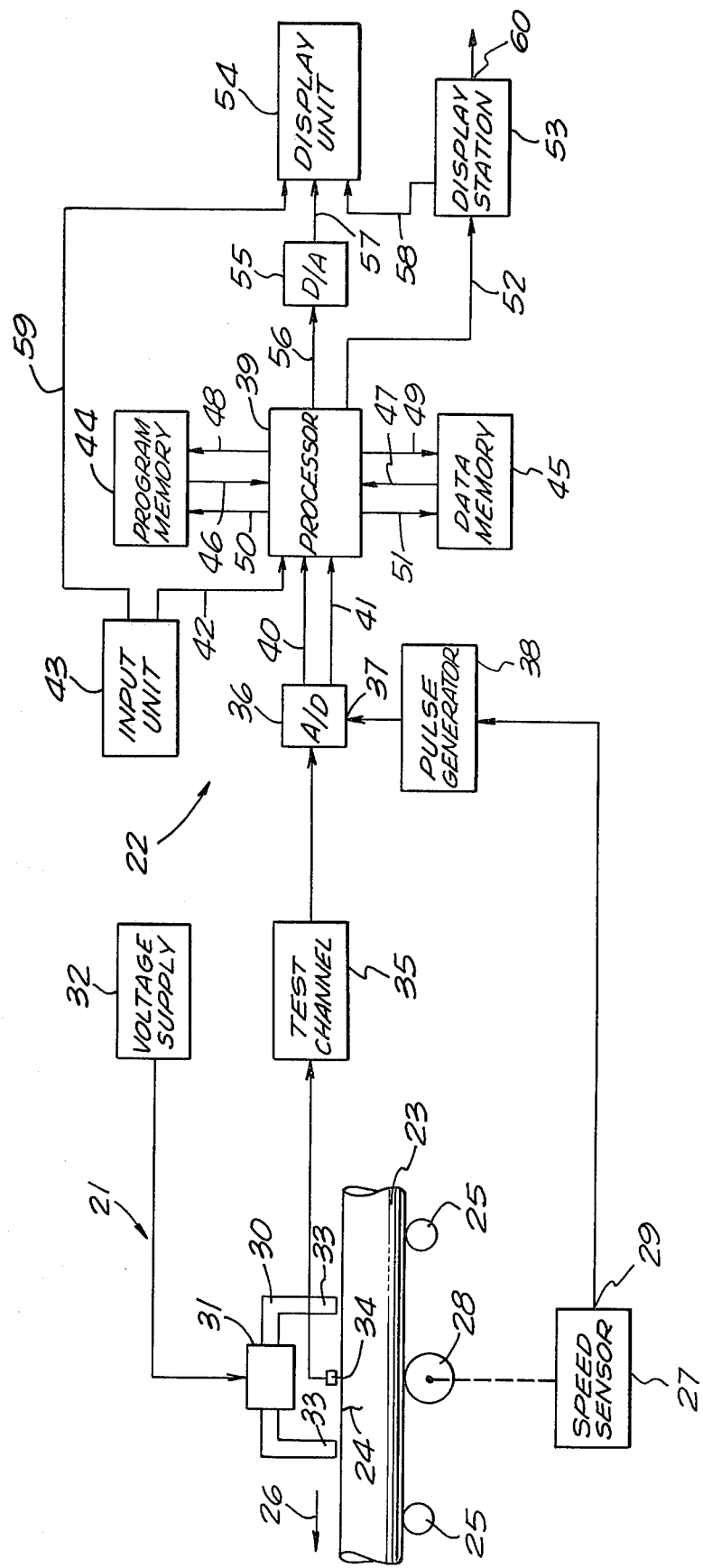
FIG. 3 is a circuit schematic of one form of apparatus for carrying out the method of this invention.

Reference is now made to FIG. 3 which shows a conventional stray flux test arrangement 21 combined with an evaluation arrangement 22 according to the invention. The test arrangement 21 serves to detect crosswise extending defects 24 in pipes 23. The pipe 23 is passed through the test arrangement 21 at a speed $V_a$, on a roller bed 25 in the direction indicated by arrow 26. A speed sensor 27 picks up the speed of the pipe 23 using a friction wheel 28 and supplies at its output 29 a signal proportional to the speed $V_a$ of the pipe. A magnet yoke 23 comprising a yoke coil 31 supplied by a supply unit 32 with a magnetizing current, magnetizes the pipe 23 in the longitudinal direction. A stray flux probe 34 arranged between the pole shoes 33 of the magnet yoke 30 scans the passing magnetized pipe 23 for magnetic defect stray fluxes. If the whole periphery of the pipe is to be scanned, the U-shaped yoke 30 shown for simplicity's sake may be replaced by a yoke surrounding the whole pipe 23, and the individual probe 34 may be replaced by a number of stray flux probes provided in circular arrangement. The signals emitted by the stray flux probe are amplified in a test channel 35 and conditioned in the known manner, for instance by means of a band-pass filter eliminating any spurious signals outside the frequency range of the defect signals. From the test channel 35, the defect signals are applied to an analog-to-digital converter 36 forming the input stage of the evaluation arrangement 22. The control input 37 of the analog-to-digital converter 36 is connected to the output of the pulse generator 38, while the input of the latter is connected to the output 29 of the speed sensor 27.

A central processing unit 39 which in the present case consists of a microprocessor controls the sequence of the evaluation operations. The central processing unit 39 is connected via a group of lines 40 and a control line 41 to the analog-to-digital converter 36, and via lines 42 to an input unit 43 comprising among other elements means for adjusting the threshold values. Also, the central processor 39 has associated with it a program memory 44 and a data memory 45 which may take the form of so-called ROM (read only memory) and a so-called RAM (random access memory), respectively. The program memory 44 contains all the necessary program elements, while the data memory 45 is available for storing any data required, and also for buffering momentary values. The groups of lines 46 and 47 (data bus) insure the data flow, the groups of lines 48 and 49 (address bus) provide for the transfer of the addresses, and the control lines 50 and 51 (control bus) transmit the control signals between the central processing unit 39 on the one hand and the two memories 44 and 45 on the other hand. The information gained is supplied by lines 52 to a display station 53 and from the latter's output 60 to other external evaluation equipment, such as color marking or grading devices. The defect signals and the defect signal thresholds are visualized by an additional display unit 54 connected via a digital-to-analog converter 55 and lines 56 and 57 to the central processing unit 39 and via additional lines 58 and 59 to the indication station 53 and the input means 43, respectively.

Signal evaluation using the arrangement shown in FIG. 3 operates as follows: The speed sensor 27 emits a voltage proportional to the speed $V_a$. In response to this voltage, the pulse generator 38 generates a frequency $f_T$ proportional to the speed $V_a$. The analog signals received from the test channel 35 are converted by the analog-to-digital converter 36 into digital signals and offered to the central processing unit 39, in synchronism with the frequency $f_T$. The input means 43 supplies the central unit 39 with the following additional information: A threshold value for large defects, a threshold value for small defects, a threshold value defining the start of the evaluation operations—this latter threshold value may be identical to the threshold value for small defects—and a threshold value for the quotient Q to decide the question "interior defect or exterior defect". An initiating signal starts a program stored in the program memory 44 to accomplish the evaluation steps described before. The information received at the indication station 53 may consist in visual indications conveying the following information:

"large exterior defect"
"small exterior defect"
"large interior defect"
"small interior defect"
"no defect"

Central unit 39—A microprocessor sold under the trade designation 8085 by Intel Corporation, Santa Clara, Calif.

Program memory 44—An electrically programmable read-only memory sold under the trade designation 2716 by Intel Corporation.

Data memory 45—A random access memory sold under the trade designation 8155 by Intel Corporation.

Digital-to-analog converter 55—One sold under the trade designation 7523 by Intel Corporation.

Display unit 54—An oscilloscope sold under the trade designation 6.710.01-12 by Institut Dr. Förster.

With the computer defined by the central processing unit 39 and associated apparatus, the described arrangement accomplished its various functions under control of the following program:

| F5 | DB | 04 | D6 | 1B | DB | 01 | C2 | 22 | 05 | 4F | C6 | 00 | FC | 98 | 05 |
|----|----|----|----|----|----|----|----|----|----|----|----|----|----|----|----|
| D3 | 08 | 2B | 2B | C3 | 44 | 05 | 21 | 30 | 04 | 06 | 02 | DB | 02 | 77 | 23 |
| DB | 01 | 77 | 23 | D7 | 05 | C2 | 05 | 05 | 23 | 36 | 1E | 97 | 23 | 77 | 23 |
| FB | 76 | C3 | 19 | 05 | 77 | 2B | 96 | 4F | 23 | 7E | 2B | 77 | DB | 04 | D6 |
| 18 | 79 | 17 | 37 | 3F | 17 | 4F | CA | 3C | 05 | D3 | 08 | C3 | 43 | 05 | C6 |
| 00 | FC | 98 | 05 | D3 | 08 | 2B | F1 | 79 | D2 | 6F | 05 | C6 | 00 | FC | 98 |
| 05 | BA | FA | 53 | 05 | 57 | 79 | 90 | FC | 98 | 05 | BB | FA | 5D | 05 | 5F |
| 41 | 35 | CA | A0 | 05 | 37 | 23 | 23 | C9 | C6 | 00 | FC | 98 | 05 | 2B | 2B |
| 2B | 2B | 2B | BE | F2 | 8B | 05 | 23 | 23 | BE | F2 | 8D | 05 | 97 | 23 | 23 |
| 23 | 23 | 23 | C9 | 23 | 23 | 41 | 57 | 1E | 00 | 37 | CE | 84 | 05 | 3D | 2F |
| C9 | 36 | 07 | 97 | 17 | 47 | 7B | 17 | BA | FA | AD | 92 | 04 | 5F | 97 | 78 |
| 35 | C2 | A3 | 05 | 2B | 78 | BE | FA | CC | 05 | 7A | 2B | BE | F2 | DD | 05 |
| 2B | BE | F2 | E2 | 05 | 97 | F0 | 05 | 7A | 2B | 2B | 2B | BE | F2 | E7 | 05 |
| 2B | BE | F2 | EC | 05 | 97 | C3 | EE | 05 | 3E | C0 | C3 | F1 | 05 | 3E | 40 |
| C3 | F0 | 05 | 3E | 03 | C3 | EF | 05 | 3E | 01 | 23 | 23 | 23 | 23 | D3 | 02 |
| DB | 02 | 77 | 23 | 36 | 1E | 97 | 23 | 23 | C9 | | | | | | |

Apart from visualizing the defect signal and the defect signal thresholds, the display unit 54 may also convey information regarding the location of the defect.

The information "interior defect—exterior defect" may be conveyed in the form of simple symbols, for instance a pulse spike pointing upwards or downwards from the defect signal threshold which may be displayed by the display unit 54 in the form of a horizontal line at the level of the defect signal threshold voltage which had been preset through the input unit 43.

To set the threshold value for the quotient Q, the following procedure is followed: Using two sample defects, namely, an interior and an exterior defect, the threshold is first set to a value which classifies both sample defects as exterior defects, and then set to a value which classifies both of them as interior defects. One notes the two settings, derives the mean value from them and sets the threshold at the mean value thus obtained.

In a practical construction of the invention, commercially available items were utilized for the correspondingly enumerated details of the arrangement:

Speed sensor 27 and pulse generator 38—A pulse wheel unit sold under the trade designation 6.799.02-2101 by Institut Dr. Förster, 7410 Reutlingen 1, F. R. Germany.

Test channel 35—A probe amplifier combined with an input amplifier both sold under the trade designations 6.031,01-6621-11 and 6.715.01-1111-13 by Institut Dr. Förster.

Analog-to-digital converter 36—One sold under the trade designation AD 7574+AD 583 by Analog Devices, Inc., Norwood, Mass.

I claim:

1. A method for evaluating a signal voltage generated by a magnetic stray flux probe uniformly scanning a magnetized test piece responsive to a defect to determine the location of the defect relative to the outer surface of the test piece, which comprises the steps of:

determining the instantaneous values of the signal voltage at n points of the defect signal mutually spaced by the same time interval, said values being determined at a time when the defect signal voltage exceeds a given threshold value;

forming the difference between each pair of neighboring instantaneous values and determining both the maximum rise difference and the maximum signal values thereof;

forming the quotient of the maximum rise difference and maximum signal values;

comparing the quotient with a predetermined threshold voltage; and continuously buffering the instantaneous values during a fixed time interval and using the buffered values when the said threshold value has been exceeded at the moment $t_o$ for determining the n values, starting with an instantaneous value obtained a given number of fixed time intervals before the time at which the defect signal exceeds the threshold value.

2. A method for evaluating a signal voltage generated by a magnetic stray flux probe uniformly scanning a magnetized test piece responsive to a defect to determine the location of the defect relative to the outer surface of the test piece, which comprises the steps of:

determining the instantaneous values of the signal voltage at n points of the defect signal mutually spaced by the same time interval;

forming the difference between each pair of neighboring instantaneous values and determining both maximum rise difference and maximum signal values;

forming the quotient of the maximum rise and maximum signal values;

comparing the quotient with a predetermined threshold voltage; and controlling the fixed time intervals by a pulse frequency derived from the scanning speed of the test piece.

3. An arrangement for determining the location of a defect in a test piece relative to the surface of the test piece in which a probe generates a signal responsive to stray field flux of the defect, comprising:

an analog-to-digital converter having input, output and control terminals having its input being connected to the defect signal voltage of the stray flux probe;

a pulse generator connected to the control input of the analog-to-digital converter to supply pulse signals for the generation of digital values at the output of the analog-to-digital converter as a function of the defect signal voltage;

sensor producing a signal proportional to the probe scanning speed connected to the pulse generator to control the pulse frequency thereof; and computer means having at least one storage means an input unit and an output unit, said input unit interconnected with the output of said converter for forming a ratio of the maximum defect signal rise with the maximum defect signal and comparing said ratio with a predetermined threshold value.

4. An arrangement for determining the location of a defect in a test piece relative to the surface of the test piece in which a probe generates a signal responsive to stray field flux of the defect, comprising:

an analog-to-digital converter having input, output and control terminals having its input being connected to the defect signal voltage of the stray flux probe;

a pulse generator connected to the control input of the analog-to-digital converter to supply pulse signals for the generation of digital values at the output of the analog-to-digital converter as a function of the defect signal voltage; and computer means connected to the output of the digital-to-analog converter for forming a ratio of the maximum defect signal rise with the maximum defect signal and comparing said ratio with a predetermined threshold value, said computer means having at least one storage means, input unit, and an output unit, said storage means serves to buffer and store instantaneous values of the defect signal voltage obtained prior to the time when the threshold value has been exceeded.

* * * * *